United States Patent
Kennedy et al.

(10) Patent No.: US 8,262,963 B2
(45) Date of Patent: Sep. 11, 2012

(54) PROCESS OF MAKING BIOABSORBABLE FILAMENTS

(75) Inventors: John Kennedy, Guilford, CT (US); Richard P. Stevenson, Colchester, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 154 days.

(21) Appl. No.: 12/817,782

(22) Filed: Jun. 17, 2010

(65) Prior Publication Data

US 2010/0292730 A1    Nov. 18, 2010

Related U.S. Application Data

(63) Continuation-in-part of application No. 10/530,076, filed as application No. PCT/US03/31360 on Oct. 2, 2003, now abandoned.

(60) Provisional application No. 60/416,087, filed on Oct. 4, 2002.

(51) Int. Cl.
  *A61B 17/04* (2006.01)
  *D01D 5/088* (2006.01)
  *D01D 5/16* (2006.01)
  *D02J 1/22* (2006.01)

(52) U.S. Cl. .............. 264/178 F; 264/210.5; 264/210.7; 264/210.8; 264/211.14; 264/211.17; 264/235.6

(58) Field of Classification Search .............. 264/178 F, 264/210.5, 210.7, 210.8, 211.14, 211.17, 264/235.6
See application file for complete search history.

(56) References Cited

U.S. PATENT DOCUMENTS

| | | | |
|---|---|---|---|
| 392,891 | A | 11/1888 | Stanwood |
| 3,106,442 | A | 10/1963 | Compostella et al. |
| 3,630,205 | A | 12/1971 | Listner |
| 4,048,256 | A | 9/1977 | Casey et al. |
| 4,243,775 | A | 1/1981 | Rosensaft et al. |
| 4,300,565 | A | 11/1981 | Rosensaft et al. |
| 4,429,080 | A | 1/1984 | Casey et al. |
| 4,438,253 | A | 3/1984 | Casey et al. |
| 4,452,973 | A | 6/1984 | Casey et al. |
| 4,891,263 | A | 1/1990 | Kotliar et al. |
| 4,911,165 | A | 3/1990 | Lennard et al. |
| 5,217,485 | A | 6/1993 | Liu et al. |
| 5,236,444 | A | 8/1993 | Muth et al. |
| 5,294,389 | A | 3/1994 | Hain et al. |
| 5,322,925 | A | 6/1994 | Muth et al. |
| 5,376,376 | A | 12/1994 | Li |
| 5,403,347 | A | 4/1995 | Roby et al. |
| 5,456,696 | A | 10/1995 | Liu |
| 5,512,291 | A | 4/1996 | Li |
| 5,554,170 | A | 9/1996 | Roby et al. |

(Continued)

FOREIGN PATENT DOCUMENTS

EP    0415783    8/1990

(Continued)

OTHER PUBLICATIONS

European Search Report for EP 03808131.1-1217 date of completion is May 29, 2009.

(Continued)

*Primary Examiner* — Leo B Tentoni

(57) ABSTRACT

Methods for making bioabsorbable copolymer filaments are provided herein. The methods include drying the polymer pellets to be extruded, melt extrusion of copolymer components, stretching the filaments in one or more draw steps and permitting the drawn filaments to relax. The copolymer preferably contains units derived from glycolide or glycolic acid and units derived from an alkylene carbonate, such as, for example, trimethylene carbonate.

23 Claims, 1 Drawing Sheet

U.S. PATENT DOCUMENTS

Figure 1:
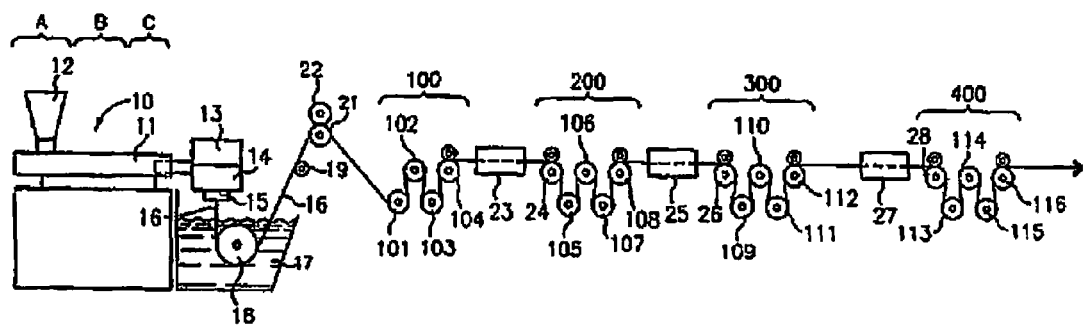

| | | |
|---|---|---|
| 5,618,313 A | 4/1997 | Roby et al. |
| 5,681,353 A | 10/1997 | Li et al. |
| 5,697,969 A | 12/1997 | Schmitt et al. |
| 5,718,716 A | 2/1998 | Goddard et al. |
| 5,735,903 A | 4/1998 | Li et al. |
| 5,797,962 A | 8/1998 | Tomihata et al. |
| RE36,370 E | 11/1999 | Li |
| 6,005,019 A | 12/1999 | Liu |
| 6,007,565 A | 12/1999 | Roby et al. |
| 6,011,121 A | 1/2000 | Goldmann et al. |
| 6,042,610 A | 3/2000 | Li et al. |
| 6,060,638 A | 5/2000 | Paul et al. |
| 6,090,910 A | 7/2000 | Shinoda et al. |
| 6,136,018 A | 10/2000 | Roby et al. |
| 6,165,202 A | 12/2000 | Kokish et al. |
| 6,191,236 B1 | 2/2001 | Roby et al. |
| 6,206,908 B1 | 3/2001 | Roby |
| 6,235,869 B1 | 5/2001 | Roby et al. |
| 6,264,674 B1 | 7/2001 | Washington et al. |
| 6,277,927 B1 | 8/2001 | Roby et al. |
| 6,287,499 B1 | 9/2001 | Roby et al. |
| 2002/0077448 A1 | 6/2002 | Antal et al. |

FOREIGN PATENT DOCUMENTS

| | | |
|---|---|---|
| EP | 0626404 | 11/1994 |
| EP | 0726078 | 9/1996 |
| EP | 0830866 | 9/1997 |
| EP | 0949299 | 3/1999 |
| EP | 0992529 | 9/1999 |
| EP | 1136511 | 9/2001 |
| EP | 1545640 A2 | 6/2005 |
| WO | WO2004/032792 | 4/2004 |

OTHER PUBLICATIONS

International Search Report for PCT/US03/31360 date of completion is Apr. 27, 2004.

Maxon Specifications, "Monofilament Polyglyconate Synthetic Absorbable Surgical Sutures," USP/EP, Except for Diameter Http://www.ussdgsutures.com/prodbyband/us_dg_sutures/specifications/maxon.html, Oct. 4, 2002.

European Search Report for EP 10251833-1219 date of completion is Mar. 7, 2011 (3 pages).

PROCESS OF MAKING BIOABSORBABLE FILAMENTS

CROSS REFERENCE TO RELATED APPLICATIONS

The present application is a continuation-in-part application claiming the benefit of and priority to U.S. application Ser. No. 10/530,076 filed on Aug. 4, 2005, now abandoned, which is a National Phase Application filed under 35 U.S.C. §371 of International Application Serial No. PCT/US2003/031360, filed Oct. 2, 2003, which claims the benefit of and priority to U.S. Provisional Application Ser. No. 60/416,087 filed on Oct. 4, 2002, the entire content of each of these Applications is incorporated herein by reference.

BACKGROUND

1. Technical Field

The present disclosure relates to methods for making copolymer filaments for use in producing surgical articles such as sutures. More particularly, this disclosure relates to filaments made from copolymers of glycolide and trimethylene carbonate that are useful in producing surgical sutures.

2. Background of Related Art

Methods for making monofilaments that are suitable surgical sutures generally include the steps of extruding a least one bioabsorbable or non-bioabsorbable polymer to provide filaments, drawing, or stretching the solidified filaments to achieve molecular orientation and annealing the drawn filaments to relieve internal stresses. See, e.g., U.S. Pat. Nos. 3,092,891, 3,106,442, 3,630,205, 4,911,165, 5,217,485 and U.K. Patent Specification No. 1,588,081 and European Patent Application No. 415,783.

It would be desirable to provide a bioabsorbable suture which exhibits good flexibility and handling characteristics while maintaining other desired characteristics, such as knot strength, knot retention and desired absorption characteristics.

SUMMARY

Methods for making bioabsorbable copolymer filaments are provided herein. The methods include drying the polymer pellets to be extruded, melt extrusion of copolymer components, stretching the filaments in one or more draw steps and permitting the drawn filaments to relax. The copolymers may contain units derived from glycolide or glycolic acid and units derived from an alkylene carbonate, such as, for example, trimethylene carbonate. The copolymers may also contain a medico-surgically useful substance.

In some embodiments, processes are described for manufacturing a monofilament suture from a block copolymer including glycolide and trimethylene carbonate. For example, some processes are described for manufacturing a monofilament suture from a block copolymer comprising from about 50 to about 80 weight percent glycolide, and about 20 to about 50 weight percent trimethylene carbonate, the process including the following: a) extruding the copolymer to provide a molten monofilament; b) quenching the molten monofilament to provide a solidified monofilament; c) drawing the solidified monofilament through a first oven maintained at a temperature of about 25° C. to about 40° C. at a draw ratio of about 2:1 to about 15:1; d) drawing the monofilament through a second oven maintained at a temperature of about 30° C. to about 150° C. at a draw ratio of about 1.1:1 to about 5:1; e) drawing the monofilament through a third oven maintained at a temperature of about 125° C. to about 165° C. at a draw ratio of about 0.5:1 to about 0.8:1; and f) annealing the monofilament.

In certain embodiments, processes are described for manufacturing a monofilament suture from a block copolymer including from about 60 to about 70 weight percent glycolide, and about 30 to about 40 weight percent trimethylene carbonate, the process including the following: a) extruding the copolymer at a temperature from about 170° C. to about 240° C. to provide a molten monofilament; b) quenching the molten monofilament in a quench bath at a temperature from about 10° C. to about 80° C. to provide a solidified monofilament; c) drawing the solidified monofilament through a first oven maintained at a temperature of about 25° C. to about 40° C. at a draw ratio of about 3:1 to about 12:1; d) drawing the monofilament through a second oven maintained at a temperature of about 30° C. to about 150° C. at a draw ratio of about 1.25:1 to about 1.50:1; e) drawing the monofilament through a third oven maintained at a temperature of about 125° C. to about 165° C. at a draw ratio of about 0.55:1 to about 0.9:1; and f) annealing the monofilament at temperatures ranging from about 100° C. to about 150° C.

In certain other embodiments, processes are also described for manufacturing a monofilament suture from a block copolymer which consists essentially of only about 50 to about 80 weight percent glycolide, and about 20 to about 50 weight percent trimethylene carbonate, the method comprising: a) extruding the copolymer to provide a molten monofilament; b) quenching the molten monofilament to provide a solidified monofilament; c) drawing the solidified monofilament through a first oven maintained at a temperature of about 25° C. to about 40° C. at a draw ratio of about 2:1 to about 15:1; d) drawing the monofilament through a second oven maintained at a temperature of about 30° C. to about 150° C. at a draw ratio of about 1.1:1 to about 5:1; e) drawing the monofilament through a third oven maintained at a temperature of about 120° C. to about 165° C. at a draw ratio of about 0.5:1 to about 0.9:1; and f) annealing the monofilament.

BRIEF DESCRIPTIONS OF THE DRAWINGS

Figure 2:

Various embodiments are described herein with reference to the drawings, wherein:

FIG. 1 shows a schematic illustration of an apparatus which is suitable for carrying out the method described herein to form a filament; and FIG. 2 shows a needled suture in accordance with this disclosure.

DETAILED DESCRIPTION

Monofilaments suitable for use as sutures are provided in accordance with the present disclosure. The monofilaments may be made from a bioabsorbable copolymer that contains glycolate units and units derived from an alkylene carbonate, such as, for example, trimethylene carbonate.

Glycolide-trimethylene carbonate copolymers from which the present filaments can be made are known to those skilled in the art. Suitable copolymers and methods for making them are disclosed, for example in U.S. Pat. Nos. 4,048,256; 4,243,775; 4,300,565; 4,429,080; and 4,438,253 the disclosures of which are incorporated herein in their entirety by this reference. In some embodiments, the filaments may be made from a block copolymer including from about 50 to about 80 weight percent glycolide and from about 20 to about 50 weight percent trimethylene carbonate. In other embodiments, the filaments may be made from a block copolymer including from about 60 to about 70 weight percent glycolide and from about 30 to about 40 weight percent trimethylene carbonate. A particularly useful composition is the glycolide-trimethylene carbonate copolymer from which the commercially available MAXON® sutures are made.

FIG. 1 schematically illustrates a monofilament suture manufacturing operation which may be suitable for producing sutures. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resin are introduced to the extruder through hopper 12. The resin is dried either before or after being placed into the hopper. The resin may be dried using any known technique. In some embodiments, the resin may be dried by flowing nitrogen gas through the resin until a desired dew point is attained. A flow rate in the range of 5 to 20 standard cubic feet per minute (scfm), in some embodiments 8 to 15 scfm, may be used. Dew points of less than about −60° C., in certain embodiments a dew point less than about −40° C. are preferred levels of drying.

Motor-driven metering pump 13 delivers melt extruded resin at a constant rate to spin pack 14 and thereafter through spinneret 15 possessing one or more orifices of desired diameter to provide a molten monofilament 16. The throughput of polymer depends upon the size of the suture being extruded and the number of spinneret openings, but generally can be in the range of about 1 to about 500 cc. In certain embodiments the throughput may be in the range of about 11 to about 306 cc. Throughput may vary depending on suture diameter and number of die holes in spinneret. Reductions in the throughput reduce the internal stresses applied to the molten monofilament during orientation. Molten monofilament 16 then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.25 to about 100 cm, in certain embodiments from about 0.5 to about 20 cm. If desired, a chimney (not shown), or shield, can be provided to isolate monofilament 16 from contact with air currents which might otherwise effect the cooling of the monofilament in an unpredictable manner. In general, barrel zone A of the extruder can be maintained at a temperature from about 170° C. to 220° C., zone B at from about 180° C. to 230° C. and zone C at from about 190° C. to about 240° C. In certain embodiments, barrel zone A of the extruder can be maintained at a temperature from about 185° C. to 205° C., zone B at from about 190° C. to 210° C. and zone C at from about 195° C. to about 215° C. Additional temperature parameters may include: metering pump block 13 at from about 180° C. to about 230° C., spin pack 14 at from about 180° C. to about 230° C., and spinneret 15 at from about 180° C. to about 230° C. Quench bath 17 may be maintained at a temperature ranging from about 10° C. to about 80° C., and in some embodiments, from about 20° C. to about 30° C.

Monofilament 16 may be passed through quench bath 17 around driven roller 18 and over idle roller 19. Optionally, a wiper (not shown) may remove excess water from the monofilament as it is removed from quench bath 17. On exiting quench bath 17 monofilament 16 is wrapped around first godet 21 provided with nip roll 22 to prevent slippage which might otherwise result from the subsequent stretching operation; and subsequently wrapped around first roll station godets 101, 102, 103 and 104 or any other suitable godet arrangement in first roll station 100. Monofilament 16 passing from first roll station 100 is stretched, e.g., with first draw ratios on the order of from about 2:1 to about 15:1; in some embodiments from about 3:1 to about 12:1; and in certain embodiments, from about 5:1 to about 7:1, to effect its orientation. Monofilament 16 is first drawn through a first heated zone 23 (e.g., hot liquid draw bath or hot air convection oven chamber) by means of second godet 24, and second roll station godets 105, 106, 107 and 108 of second roll station 200 or any other suitable arrangement of godets which rotate at a higher speed than first godet 21 and first roll station godets 101, 102, 103, and 104 to provide the desired first draw ratio. The temperature of first heated zone 23 may range from about 20° C. to about 90° C., and in certain embodiments, may range from about 25° C. to about 40° C.

The first draw ratios described herein may be altered by changing the speeds of any of first godet 21 and first roll station godets 101, 102, 103, and 104 of first roll station 100. For example, in some embodiments, first godet 21 may be maintained at a speed of about 2 meters/minute or "mpm" ($G_1$) and second godet 24 may be maintained at a speed of about 10 mpm ($G_2$) to provide a first draw ratio of about 5:1 ($G_2/G_1$). In certain embodiments, the speed of second godet 24 may be set and may not be changed at a speed ranging from about 5 mpm to about 15 mpm; and in some embodiments from about 9 mpm to about 10 mpm. In such embodiments, the speed of first godet 21 may range from about 1 mpm to about 5 mpm; and in some embodiments, may range from about 1.5 mpm to about 2.5 mpm.

Even minor changes in the speed of first godet 21 may alter several of the tensile characteristics, i.e., knot-pull strength, elongation, modulus, and in-vitro strength, of the monofilament. For example, reduction of the speed of first godet 21 by increments of about 0.1 mpm may decrease knot pull values, elongation values, and in-vitro values, but may increase the modulus value of the monofilament. Conversely, increases in the speed of first godet 21 by increments of about 0.1 mpm may increase knot pull values, elongation values, and in-vitro values, but may decrease the modulus value of the monofilament.

Returning to FIG. 1, monofilament 16 may be subjected to a second draw after passing second roll station godets 105, 106, 107 and 108. Specifically, monofilament 16 passing from second roll station 200 may be stretched, e.g., with draw ratios on the order of from about 1.1:1 to about 5:1; in some embodiments from about 1.2:1 to about 3:1; in some other embodiments from about 1.25:1 to about 1.5:1, to effect its further orientation. Monofilament 16 may be drawn through a second heated zone 25 (e.g., hot liquid draw bath or hot air convection oven chamber) by means of third godet 26 and third roll station godets 109, 110, 111, and 112 of third roll station 300, or any other suitable arrangement of godets which rotate at a higher speed than second godet 24 and second roll station godets 105, 106, 107, and 108 to provide the desired draw ratio. The temperature of second heated zone 25 may advantageously range from about 30° C. to about 150° C., and in some embodiments, may range from about 110° C. to about 120° C.

The second draw ratios described herein may be altered by changing the speeds of any of third godet 26 and third roll station godets 109, 110, 111, and 112 of third roll station 300. For example, in some embodiments, third godet 26 may be maintained at a speed of about 13.5 mpm ($G_3$) and second godet 24 may be maintained at a speed of about 9.5 mpm ($G_2$) to provide a second draw ratio of about 1.42:1 ($G_3/G_2$). In certain embodiments, the speed of second godet 24 may be set and may not be changed at a speed ranging from about 5 mpm to about 15 mpm; and in some embodiments from about 9 mpm to about 10 mpm. In such embodiments, the speed of third godet 26 may range from about 5.5 mpm to about 25 mpm; and in some embodiments, may range from about 13 mpm to about 16 mpm.

Even minor changes in the speed of third godet 26 may alter the in-vitro strength of the monofilament. For example, reduction of the speed of third godet 26 by increments of about 0.2 mpm may decrease in-vitro tensile values of the monofilament. Conversely, increases in the speed of third godet 26 by increments of about 0.1 mpm may increase in-vitro tensile values of the monofilament. In embodiments, knot pull values, elongation values, and modulus may not be affected by such minor changes in speed of third godet 26.

Following the second draw, monofilament 16 may be subjected to a third draw after passing third roll station godets 109, 110, 111 and 112. Specifically, monofilament 16 passing from third roll station 300 may be relaxed, e.g., with draw ratios on the order of from about 0.5:1 to about 0.9:1; in some embodiments from about 0.55:1 to about 0.8:1, to eliminate the potential for material "creep" and increase the tensile elongation of the monofilament. Monofilament 16 may be drawn through a third heated zone 27 (e.g., hot liquid draw bath or hot air convection oven chamber) by means of fourth godet 28 and fourth roll station godets 113, 114, 115, and 116 of fourth roll station 400, or any other suitable arrangement of godets which rotate at a lower speed than third godet 26 and third roll station godets 109, 110, 111, and 112 to provide the desired draw ratio. The temperature of third heated zone 27 may advantageously range from about 125° C. to about 165° C., and in some embodiments, may range from about 128° C. to about 150° C. In still other embodiments, the temperature of third heated zone 27 may advantageously be maintained at about 130° C.

The third draw ratios described herein may be altered by changing the speeds of any of fourth godet 28 and fourth roll station godets 113, 114, 115, and 116 of fourth roll station 400. For example, in some embodiments, fourth godet 28 may be maintained at a speed of about 9.9 mpm ($G_4$) and third godet 26 may be maintained at a speed of about 13.5 mpm ($G_3$) to provide a third draw ratio of about 0.73:1 ($G_4/G_3$). In certain embodiments, the speed of fourth godet 28 may range from about 3 mpm to about 15 mpm; and in some embodiments, may range from about 8 mpm to about 10 mpm.

The speeds of fourth godet 28 may be changed to alter the tensile characteristics of the monofilament. For example, reduction of the speed of fourth godet 28 by increments of about 0.1 mpm may increase knot pull values, elongation values, but may decrease the modulus value of the monofilament. Conversely, increases in the speed of fourth godet 28 by increments of about 0.1 mpm may decrease knot pull values, elongation values, but may increase the modulus value of the monofilament.

The total draw ratio for monofilament 16 may range from about 5:1 to about 10:1; in some embodiments from about 6.5:1 to about 8.5:1; and in other embodiments from about 7:1 to about 8:1. In embodiments, the draw rate payoff may range from about 5 meters/minute (mpm) to about 70 meters/minute; in some embodiments, the draw rate payoff may range from about 8 mpm to about 60 mpm.

Suitable parameters for spinning and drawing monofilaments made according to the present disclosure may be summarized in any of Tables I-III below. Some of the parameters may vary according to the size of the monofilament being spun and drawn. For example, Tables I, II, and III represent the parameters suitable for forming a size 0, 1, and 2/0 filament, respectively, each made from a glycolide-trimethylene carbonate copolymer according to the present disclosure.

TABLE I

| | Filament Size 0 |
|---|---|
| Extruder Profile | |
| Feed Cooling | On |
| Barrel temp., ° C., zone A | 195 (190-200) |
| Barrel temp., ° C., zone B | 200 (195-205) |
| Barrel temp., ° C., zone C | 200 (195-205) |
| Clamp temp., ° C. | 200 (195-205) |
| Adapter temp., ° C. | 200 (195-205) |
| Block temp., ° C. | 200 (195-205) |
| Die temp., ° C. | 200 (195-205) |
| Aux. Die temp., ° C. | 225 (220-230) |
| Barrel melt temp., ° C. | Monitor Only |
| Pump melt temp., ° C. | Monitor Only |
| Die melt temp., ° C. | Monitor Only |
| Barrel pressure, psi | Monitor Only |
| Pre-Pump pressure, psi | 350-2000 |
| Die pressure, psi | Monitor Only |
| Extruder screw, rpm | Auto |
| Pump, rpm | Monitor Only |
| Quench Bath temp., ° C. | 22 |
| Air Gap (cm) | 1 |
| Pump (cc/rev) 0.297 Pump (Only) | |
| Resin Viscosity 1.13-1.68 dl/g in | |
| Resin Dew Point ≦−60° C. | |
| Die filtration 20μ | |
| Draw Conditions | |
| Driven R, mpm | 0 |
| Roll Depth, cm | (37-48) |
| First godet, mpm | 1.85 (1.8-1.9) |
| Second godet, mpm | 9.5 |
| Third godet, mpm | 13.5 (13.4-13.6) |
| Forth godet, mpm | 9.9 |
| First oven temp., ° C. | 30 |
| Second oven temp., ° C. | 115 |
| Third oven temp., ° C. | 130 |
| Draw ratio #1 | 5:14:1 (5.0:1-5.28:1) |
| Draw ratio #2 | 1.42:1 (1.41:1-1.43:1) |
| Draw ratio #3 | 0.733:1 (0.728:1-0.739:1) |
| Total Draw | 7.30 (7.05:1-7.56:1) |
| Purge Time | 3 hrs |

TABLE 2

| | Filament Size 1 |
|---|---|
| Extruder Profile | |
| Feed Cooling | On |
| Barrel temp., ° C., zone A | 200 (190-200) |
| Barrel temp., ° C., zone B | 205 (195-205) |
| Barrel temp., ° C., zone C | 205 (195-205) |
| Clamp temp., ° C. | 205 (195-205) |
| Adapter temp., ° C. | 205 (195-205) |
| Block temp., ° C. | 205 (195-205) |
| Die temp., ° C. | 208 (206-210) |
| Aux. Die temp., ° C. | 226 (221-230) |
| Barrel melt temp., ° C. | Monitor Only |
| Pump melt temp., ° C. | Monitor Only |
| Die melt temp., ° C. | Monitor Only |
| Barrel pressure, psi | Monitor Only |
| Pre-Pump pressure, psi | 350-2000 |
| Die pressure, psi | Monitor Only |
| Extruder screw, rpm | Auto |
| Pump, rpm | Monitor Only |
| Quench Bath temp., ° C. | 22 |
| Air Gap (cm) | 1 |
| Pump (cc/rev) 0.297 Pump (Only) | |
| Resin Viscosity 1.13-1.68 dl/g in | |
| Resin Dew Point ≦−60° C. | |
| Die filtration 20μ | |

TABLE 2-continued

| | Filament Size 1 |
|---|---|
| Draw Conditions | |
| Driven R, mpm | 0 |
| Roll Depth, cm | (37-48) |
| First godet, mpm | 1.85 (1.8-1.9) |
| Second godet, mpm | 9.5 |
| Third godet, mpm | 13.5 (13.4-13.6) |
| Forth godet, mpm | 9.6 (9.5-10.0) |
| First oven temp., ° C. | 30 |
| Second oven temp., ° C. | 115 |
| Third oven temp., ° C. | 130 |
| Draw ratio #1 | 5:14:1 (5.0:1-5.28:1) |
| Draw ratio #2 | 1.42:1 (1.41:1-1.43:1) |
| Draw ratio #3 | 0.711:1 (0.699:1-0.746:1) |
| Total Draw | 7.30 (7.05:1-7.56:1) |
| Purge Time | 2 hrs |

TABLE 3

| | Filament Size 2/0 |
|---|---|
| Extruder Profile | |
| Feed Cooling | On |
| Barrel temp., ° C., zone A | 195 (190-200) |
| Barrel temp., ° C., zone B | 200 (195-205) |
| Barrel temp., ° C., zone C | 200 (195-205) |
| Clamp temp., ° C. | 200 (195-205) |
| Adapter temp., ° C. | 200 (195-205) |
| Block temp., ° C. | 200 (195-205) |
| Die temp., ° C. | 200 (195-205) |
| Aux. Die temp., ° C. | 220 (220-230) |
| Barrel melt temp., ° C. | Monitor Only |
| Pump melt temp., ° C. | Monitor Only |
| Die melt temp., ° C. | Monitor Only |
| Barrel pressure, psi | Monitor Only |
| Pre-Pump pressure, psi | 350-2000 |
| Die pressure, psi | Monitor Only |
| Extruder screw, rpm | Auto |
| Pump, rpm | Monitor Only |
| Quench Bath temp., ° C. | 22 |
| Air Gap (cm) | 1 |
| Pump (cc/rev) 0.297 Pump (Only) | |
| Resin Viscosity 1.13-1.68 dl/g in | |
| Resin Dew Point ≦−60° C. | |
| Die filtration 20μ | |
| Draw Conditions | |
| Driven R, mpm | 0 |
| Roll Depth, cm | (37-48) |
| First godet, mpm | 1.75 (1.7-1.8) |
| Second godet, mpm | 10 |
| Third godet, mpm | 13.2 (13.1-13.3) |
| Forth godet, mpm | 9.2 (9.1-9.5) |
| First oven temp., ° C. | 30 |
| Second oven temp., ° C. | 115 |
| Third oven temp., ° C. | 130 |
| Draw ratio #1 | 5:85:1 (5.56:1-5.88:1) |
| Draw ratio #2 | 1.32:1 (1.31:1-1.33:1) |
| Draw ratio #3 | 0.697:1 (0.684:1-0.725:1) |
| Total Draw | 7.71 (7.28:1-7.84:1) |
| Purge Time | 4.2 hrs |

In other embodiments, the annealing process may performed off-line, wherein monofilament 16 may be wound as a single layer around a large drum, with or without vacuum and/or pressure, at a temperature ranging from about 100° C. to about 150° C.; in some embodiments, from about 120° C. to about 130° C. The large drums may be purged with nitrogen gas. The annealing process may last from about 9 to about 24 hours; in some embodiments from about 12 to 18 hours. In such embodiments, increasing the cycle time and/or decreasing the annealing temperature may achieve full crystallization, monomer removal and internal stress reduction of monofilament 16 without exposing monofilament 16 to temperatures near the melting point of the materials used to make monofilament 16, i.e., about 185° C. Also, a single layer of material on the annealing drum eliminates the possibility of cross wind dents which may occur where monofilaments may be overlapped or multilayered, thus yielding a better monofilament.

The suture as described herein, suture 501, may be attached to a surgical needle 500 as shown in FIG. 2 by methods well known in the art. Wounds may be sutured by passing the needled suture through tissue to create wound closure. The needle may then be removed from the suture and the suture tied.

It is further within the scope of the present disclosure to incorporate one or more medico-surgically useful substances into the present disclosure, e.g., those which accelerate or beneficially modify the healing process when particles are applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

Examples of classes of therapeutic agents, which may be utilized in accordance with the present disclosure include, for example, anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of therapeutic agents may be used.

Suitable antimicrobial agents which may be included as a therapeutic agent include, for example, triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a therapeutic agent.

Other examples therapeutic agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable therapeutic agents, which may be included in the monofilament include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

It is also contemplated that it may be desirable to dye the sutures of the present disclosure in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Such sutures, in accordance with the present disclosure, may be dyed by adding up to about a few percent, and in some embodiments, about 0.2% dye, such as D&C Violet No. 2 to the resin prior to extrusion.

While the above description contains many specifics and examples, these specifics and examples should not be construed as limitations on the scope of the present disclosure, but merely as exemplifications of detailed embodiments thereof. Those skilled in the art will envision many other possible variations that are within the scope and spirit of the present disclosure.

What is claimed is:

1. A process for manufacturing a monofilament suture from a block copolymer comprising from about 50 to about 80 weight percent glycolide, and about 20 to about 50 weight percent trimethylene carbonate, the method comprising: a) extruding the copolymer to provide a molten monofilament; b) quenching the molten monofilament to provide a solidified monofilament; c) drawing the solidified monofilament through a first oven maintained at a temperature of about 25° C. to about 40° C. at a draw ratio of about 2:1 to about 15:1; d) drawing the monofilament through a second oven maintained at a temperature of about 30° C. to about 150° C. at a draw ratio of about 1.1:1 to about 5:1; e) drawing the monofilament through a third oven maintained at a temperature of about 125° C. to about 165° C. at a draw ratio of about 0.5:1 to about 0.8:1; and f) annealing the monofilament.

2. The process of claim 1 wherein the step of extruding the copolymer comprises extruding the copolymer at a temperature from about 170° C. to about 240° C.

3. The process of claim 1 wherein the step of quenching the molten monofilament comprises utilizing a quench bath at a temperature from about 10° C. to about 80° C.

4. The process of claim 1 wherein the step of quenching the molten monofilament comprises utilizing a quench bath at a temperature from about 20° C. to about 30° C.

5. The process of claim 1 wherein the step of drawing the solidified monofilament through the first oven comprises drawing at a draw ratio of about 3:1 to about 12:1.

6. The process of claim 1 wherein the step of drawing the solidified monofilament through the first oven comprises drawing at a draw ratio of about 5:1 to about 7:1.

7. The process of claim 1 wherein the step of drawing the solidified monofilament through the second oven comprises drawing at a draw ratio of about 1.2:1 to about 3:1.

8. The process of claim 1 wherein the step of drawing the solidified monofilament through the second oven comprises drawing at a draw ratio of about 1.25:1 to about 1.5:1.

9. The process of claim 1 wherein the step of drawing the solidified monofilament through the third oven comprises drawing at a draw ratio of about 0.55:1 to about 0.75:1.

10. The process of claim 1 wherein the total draw ratio is from about 6.5:1 to about 8.5:1.

11. The process of claim 1 wherein the total draw ratio is from about 7:1 to about 8:1.

12. The process of claim 1 wherein the draw rate payoff may range from about 5 meters/minute to about 70 meters/minute.

13. The process of claim 1 wherein the step of drawing the solidified monofilament through the third oven comprises drawing the monofilament through a third oven maintained at a temperature of about 128° C. to about 150° C.

14. The process of claim 1 wherein the step of annealing the monofilament comprises subjecting the monofilament to temperatures ranging from about 100° C. to about 180° C.

15. The process of claim 1 wherein the step of annealing the monofilament comprises subjecting the monofilament to temperatures ranging from about 110° C. to about 150° C.

16. The process of claim 1 wherein the step of annealing lasts from about 9 to about 24 hours.

17. The process of claim 1 wherein the monofilament suture further comprises at least one medico-surgically useful substance.

18. The process of claim 1 wherein the at least one medico-surgically useful substance comprises a growth promoting factor.

19. The process of claim 1 wherein the at least one medico-surgically useful substance comprises an antimicrobial agent.

20. A process for manufacturing a monofilament suture from a block copolymer comprising from about 60 to about 70 weight percent glycolide, and about 30 to about 40 weight percent trimethylene carbonate, the method comprising: a)

extruding the copolymer at a temperature from about 170° C. to about 240° C. to provide a molten monofilament; b) quenching the molten monofilament in a quench bath at a temperature from about 10° C. to about 80° C. to provide a solidified monofilament; c) drawing the solidified monofilament through a first oven maintained at a temperature of about 25° C. to about 40° C. at a draw ratio of about 3:1 to about 12:1; d) drawing the monofilament through a second oven maintained at a temperature of about 30° C. to about 150° C. at a draw ratio of about 1.25:1 to about 1.50:1; e) drawing the monofilament through a third oven maintained at a temperature of about 125° C. to about 165° C. at a draw ratio of about 0.55:1 to about 0.91:1; and f) annealing the monofilament at temperatures ranging from about 100° C. to about 150° C.

21. A process for manufacturing a monofilament suture from a block copolymer consisting essentially of about 50 to about 80 weight percent glycolide, and about 20 to about 50 weight percent trimethylene carbonate, the method comprising: a) extruding the copolymer to provide a molten monofilament; b) quenching the molten monofilament to provide a solidified monofilament; c) drawing the solidified monofilament through a first oven maintained at a temperature of about 25° C. to about 40° C. at a draw ratio of about 2:1 to about 15:1; d) drawing the monofilament through a second oven maintained at a temperature of about 30° C. to about 150° C. at a draw ratio of about 1.1:1 to about 5:1; e) drawing the monofilament through a third oven maintained at a temperature of about 120° C. to about 165° C. at a draw ratio of about 0.5:1 to about 0.9:1; and f) annealing the monofilament.

22. The process of claim 20, wherein the block copolymer comprises from about 65 to about 67 weight % glycolide and about 33 to about 35 weight % trimethylene carbonate.

23. The process of claim 21, wherein the block copolymer comprises from about 65 to about 67 weight % glycolide and about 33 to about 35 weight % trimethylene carbonate.

\* \* \* \* \*